United States Patent [19]

Binninger

[11] 3,966,927

[45] June 29, 1976

[54] METHODS FOR INDUCING PARTURITION IN CATTLE WITH CERTAIN INTRAVENOUSLY-INJECTED SYNTHETIC GLUCOCORTICOIDS

[76] Inventor: Clarence E. Binninger, Box 1952, Orofino, Idaho 83544

[22] Filed: Dec. 16, 1974

[21] Appl. No.: 532,769

[52] U.S. Cl. .............................. 424/243; 424/241
[51] Int. Cl.² ................... A61K 31/56; A61K 31/58
[58] Field of Search ........................... 424/243, 241

[56] References Cited
UNITED STATES PATENTS

| | | | |
|---|---|---|---|
| 3,743,730 | 7/1973 | Adams | 424/243 |
| 3,775,539 | 11/1973 | Anderson | 424/243 |
| 3,856,955 | 12/1974 | Anderson | 424/243 |

OTHER PUBLICATIONS

Adams, J.A.V.M.A. 154(3): 251–265 (1969) "The Elective Induction of Labor and Parturition in Cattle". Adams et al., J.A.V.M.A. 154(11): 1396–1397 (1967) "The Elective Induction of Parturition in Cattle, Sheep and Rabbits".

*Primary Examiner*—Shep K. Rose

[57] ABSTRACT

Methods employing compositions containing a long-acting glucocorticoid, as for example, dexamethasone trimethylacetate, for inducing parturition in cattle up to four to six weeks prior to normal birth and within two to three days after intravenous administration of the glucocorticoid, with low incidence of retention of placenta, in-utero and post partum mortality and high rate of efficacy and parturition synchronization.

3 Claims, No Drawings

METHODS FOR INDUCING PARTURITION IN CATTLE WITH CERTAIN INTRAVENOUSLY-INJECTED SYNTHETIC GLUCOCORTICOIDS

DETAILED DISCLOSURE

This invention relates to induction of parturition in bovine animals and more particularly to methods for inducing parturition in cows with certain synthetic glucocorticoids administered intravenously.

Synthetic glucocorticoids or corticosteroids, such as prednisolone, dexamethasone, flumethasone, triamcinolone acetonide, dexamethasone trimethylacetate, etc., have been widely used in the veterinary field as anti-inflammatory agents and for the treatment of bovine ketosis. These compounds have been classified according to the relative duration of therapeutic effect into short-acting and long-acting corticosteroids, the former being exemplified by prednisolone and dexamethasone and the latter, by triamcinolone acetonide and dexamethasone trimethylacetate. Short-acting glucocorticoids at first and then also long-acting glucocorticoids were found to be effective also for parturition induction in farm animals. (Adams, The Elective Induction of Labor and Parturition in Cattle, J.A.V.M.A., 154 (3), 251-65, 1969; Adams et al., The Elective Induction of Parturition in Cattle, Sheep and Rabbits, J.A.V.-M.A., 154 (11), 1396-97, 1969; and U.S. Pat. No. 3,775,539, issued Nov. 27, 1973.) Glucocorticoid-induced parturition was heralded by investigators and widely used by veterinarians, especially, in New Zealand and Australia, as a highly useful tool in animal husbandry and the dairy and beef industry. Applying these methods, veterinarians could indeed advance calving during the last few weeks or even months of gestation by an intramuscular injection of a glucocorticoid.

However, an extremely high incidence of retained fetal membranes was a consistent and serious drawback in practicing parturition induction in cattle by employing short-acting glucocorticoids. More specifically, it was found that in the vast majority of cases the fetal membranes were retained with resultant serious uterine problems, e.g., purulent metritis or endometritis. Also, massive outbreaks of milk fever were encountered in this practice. Furthermore, in practicing such parturition induction the rate of success turned out to be most erratic and unpredictable with a failure rate of up to 90%, that is, calving failed to occur within two to three days which is the normal period within which short-acting glucocorticoids induce parturition and the treated cows calved after their normal gestation period as though no induction had been attempted. These undesirable side-effects and serious drawbacks existed even if parturition induction was practiced at a relatively late stage of pregnancy, i.e., even in the last month of gestation, the possible exception being the last two weeks of normal gestation.

Parturition-induction methods employing long-acting glucocorticoids as disclosed in U.S. Pat. No. 3,775,539, represented a considerable advance and improvement over analogous methods with short-acting parturition-inducing agents because they were not beset by such undesirable and serious side-effects and drawbacks as very high incidence of placenta retention and very poor efficacy rate in causing parturition earlier than two weeks before natural parturition. However, other problems surfaced with this long-acting glucocorticoid induction practice. For instance, there was observed an increased incidence of post-partum (within 24 hours) mortality as well as of in utero fetal mortality with a fetus being born which had been dead for 2 to 3 days and which was completely enclosed within the placenta. Another drawback is poor parturitiion synchronization, that is, lack of constancy of the latent period or unpredictability of parturition following a parturition-inducing treatment. The latent period, which is the time interval between the administration of a parturition-inducing treatment and the actual time of parturition, varies widely between one to three weeks.

However, parturition induction and synchronization in cattle presents great economic incentives. Significant economic benefits and advantages would accrue if bovine parturition induction without the above-mentioned undesirable side-effects and serious problems were possible. Accordingly, it is a major object of this invention to overcome these side-effects and problems by providing improved methods and compositions for parturition induction in cattle. Another important object of this invention is to induce parturition in cows which otherwise approximates natural birth and has little adverse effect on the calving process and the viability of the fetus and the calf and the health, lactation and fertility of the cow. Yet another object is to synchronize bovine parturition induced as early as four to six weeks before normal birth without serious side-effects and complications. Other objects will become apparent from the following disclosure.

Surprisingly and unexpectedly, it has now been found that the above-mentioned objects can be accomplished by methods employing certain intravenously-injected long-acting glucocorticoids to induce and synchronize parturition very consistently and without the undesirable side-effects, such as, in particular, retained fetal membranes and in-utero and post-partum mortality which commonly accompany the above-noted prior art methods.

This new technique for bovine parturition induction thus yields the following special advantages: 1. reduction in the incidence of retention of placenta, 2. reduction in the incidence of fetal and calf mortality, 3. high degree of predictability of the time of parturition (synchronization), and 4. increase in labor efficiency due to the shorter calving intervals.

In greater detail the present inventive method involves the intravenous administration of a parturition inducing agent, as for example, preferably, dexamethasone-21-trimethylacetate (21-trimethylacetate of $\Delta^{1,4}$-16$\alpha$-methyl-9$\alpha$-fluoro-pregnadiene-11$\beta$:17$\alpha$:21-triol-3:20-dione or 16$\alpha$-methyl9$\alpha$-fluoroprednisolone trimethylacetate, hereinafter "dexamethasone trimethylacetate") which had heretofore been known as a highly active anti-inflammatory glucocorticoid with protracted effect.

According to the concept of this invention, dexamethasone trimethylacetate can be intravenously administered to cows, at least about 235 days pregnant, i.e., within up to four to six weeks of natural calving. This potential shortening of the pregnancy represents a very significant economic benefit and advantage. The latent period in this parturition-induction method is thus only two to three days.

According to the concept of this invention, the parturition inducing agent is administered intravenously and the effective dosage of parturition inducing agent can range between about 10 and 60 mg. The preferred dosage range employed is conveniently between about 20 and 40 mg. The actual dosage used in initial series of experiments was 20 mg and 25 mg. Although the choice of dosage is not specifically related to body size, it may be influenced as will be apparent to men skilled in the art by the size of the animal as well as its physical composition, the stage of gestation, the number of previous offsprings, etc.

The dosage unit form for intravenous administration will preferably be a microcrystalline suspension of the parturition-inducing agent, e.g., dexamethasone trimethylacetate, with the suspension containing the dexamethasone trimethylacetate in an isotonic and stabilized aqueous solution. It will be appreciated, of course, by men skilled in the art that any other equivalent can be employed and is within the scope of this invention. The effectiveness in inducing parturition in cows according to the concept of this invention without abnormal incidence of retention of placenta and fetal and calf mortality was demonstrated and illustrated by results obtained in the following series of experiments.

EXAMPLE 1

To a group of cows managed by Bob Hannon in Holbrook, N.S.W. Australia, a dose of 25 mg of dexamethasone trimethylacetate in the form of 0.5% microcrystalline suspension was injected intravenously. The following are the details:

| Cow No. | Estimated Days before Term | Latent Period (days) | Calf Condition | Type of Birth | Cow Complications |
|---|---|---|---|---|---|
| H-1 | 15–21 | 2 | Live | Normal | None |
| 1556 | 7 | 2 | Live | Normal | None |
| 1555 | 12 | 2 | Live | Assisted | None |
| 1565 | 10–14 | 2 | Live | Normal | None |
| 1562 | 14 | 1 | Live | Assisted | None |
| 1597 | 7 | 1 | Live | Normal | None |
| 1553 | 8–10 | 2 | Live | Normal | None |
| 1589 | 14 | 1 | Live | Assisted | None |
| 1588 | 12 | 2 | Live | Normal | None |
| 1579 | 7–10 | 2 | Live | Normal | Retained Placenta |
| 1557 | <21 | 3 | Live | Normal | Retained Placenta |
| 1582 | 21 | 2 | Live | Assisted | None |
| 1594 | 18 | 2 | Live | Assisted | None |
| 1542 | <21 | 4 | Live | Normal | Retained Placenta |
| 1586 | 5 | 1 | Dead | Assisted | None |
| 1526 | 7 | 2 | Live | Assisted | Retained Placenta |

EXAMPLE 2

In a similar manner 20 mg were administered to a group of cows owned by Tim Watson of Culcairn, NSW, the results being the following:

| Cow No. | Estimated Days before Term | Latent Period (days) | Calf Condition | Type of Birth | Cow Complications |
|---|---|---|---|---|---|
| TW-1 | 7 | 2 | Born Live but died | Ceasarian | None |
| TW-2 | 7 | 2 | Live | Assisted | None |
| TW-3 | 21–30 | 2 | Live | Normal | None |
| TW-4 | 21–30 | 2 | Live | Assisted | None |
| TW-5 | 14–21 | 2 | Live | Normal | Retained Placenta (Shed Later) 48 hrs. |
| TW-6 | 14–21 | 3 | Live | Assisted | None |
| TW-7 | 21–30 | 3 | Born Live but died | Assisted | None |

EXAMPLE 3

Again in a similar manner, 20 mg were administered intravenously to a number of cows in the Clem King herd in the Holbrook area with the following results.

| Cow No. | Estimated Days before Term | Latent Period (days) | Calf Condition | Type of Birth | Cow Complications |
|---|---|---|---|---|---|
| CK-1 | 30 | 2 | Live | Assisted* | None |
| CK-2 | 7–10 | 2 | Live | Assisted | None |
| CK-3 | 31 | 2 | Live | Assisted | None |
| CK-4 | 10 | 2 | Live | Assisted | None |
| CK-5 | 10 | 2 | Live | Assisted | None |
| CK-6 | 14 | 2 | Live | Assisted | Retained Placenta |
| CK-7 | 10 | 2 | Live | Assisted | None |
| CK-8 | 21 | 2 | Live | Assisted | None |
| CK-9 | 10–14 | 3 | Live | Assisted | None |
| CK-10 | 14 | 3 | Born Live but died | Assisted (slow delivery) | Retained Placenta |
| CK-11 | 21–30 | 2 | Live | Assisted | Retained Placenta (Cow Sick) |
| CK-12 | <7 | 2 | Live | Assisted | None |
| CK-13 | 10–14 | 2 | Live | Assisted | None |
| CK-14 | <10 | 2 | Live | Assisted | None |
| CK-15 | <10 | 4 | Live | Assisted | None |

*All births were assisted as owner desired to pull each calf as soon as cow showed signs of strain.

These findings and observations translate into tremendous benefits to the dairy and beef industry and especially to the farmer. More specifically, early and synchronized parturition induction is particularly useful if the feed supplies are seasonal or if the management of the herd is made difficult by late births. An example is the situation in New Zealand where calving in milking herds is undesirable after October 1. Also the rearing of calves born late is more problematic. Furthermore, first heifers and cows which have difficulties and traumas in calving can be subjected to early parturition induction in accordance with this invention which is a further obvious economic advantage.

Apart from its function as a management tool in animal husbandry and apart from the significant economic benefits, early parturition induction may also and secondarily be resorted to for medical reasons, e.g. to terminate gestations which have run too far over their time, to control fetal development where gross fetal oversize could be expected to cause dystocia at full term parturition, in cases of acute and chronic traumatic reticulitis, circulatory incompetence with bronchial pneumonia, pregnancy toxemia, amniotic dropsy (hydrops), kidney diseases, fractures etc.

While the invention has been illustrated and its effectiveness demonstrated by particular reference to dexamethasone trimethylacetate as parturition-inducing agent and while dexamethasone trimethylacetate represents the preferred parturition-inducing agent, it has also been found that other similarly active and analogous synthetic glucocorticoids can be employed in the practice of this invention.

Examples of such other long-lasting glucocorticoids are the congener esters of dexamethasone trimethylacetate described and claimed in U.S. Pat. No. 3,375,261. Moreover, further examples of effective glucocorticoid-21-esters are dexamethasone-21-isonicotinate, dexamethasone-21-cyclohexylacetate, dexamethasone-17,21-dipropionate, etc. Still further examples are the 21-esters of triamcinolone and the acetonides thereof.

What is claimed is:

1. In a method of bovine parturition induction with synthetic glucocorticoids, the improvement which consists in intravenously administering to cows, pregnant for at least about 235 days, 10 to 60 mg of a long-lasting parturition-inducing 21-esterified glucocorticoid whereby parturition with low incidence of retained placenta and in-utero fetal and post-partum calf mortality takes place in about two to three days.

2. A method according to claim 1 wherein said long-lasting parturition-inducing 21-esterified glucocorticoid is dexamethasone 21-trimethylacetate.

3. A method according to claim 2 wherein 20 to 40 mg of dexamethasone trimethylacetate is administered intravenously.

* * * * *